(12) United States Patent
Baumann et al.

(10) Patent No.: US 8,683,628 B2
(45) Date of Patent: Apr. 1, 2014

(54) PATIENT SUPPORT TABLE

(75) Inventors: Berthold Baumann, Kastl (DE); Peter Bier, Gremsdorf (DE); Franz Dirauf, Ebensfeld (DE); Dieter Heinl, Erbendorf (DE)

(73) Assignee: Siemens Aktiengesellschaft, München (DE)

( * ) Notice: Subject to any disclaimer, the term of this patent is extended or adjusted under 35 U.S.C. 154(b) by 902 days.

(21) Appl. No.: 11/707,437

(22) Filed: Feb. 16, 2007

(65) Prior Publication Data
US 2007/0200396 A1 Aug. 30, 2007

(30) Foreign Application Priority Data
Feb. 23, 2006 (DE) .................. 10 2006 008 505

(51) Int. Cl.
*A47B 13/00* (2006.01)

(52) U.S. Cl.
USPC ................. 5/601; 297/135; 5/600; 5/616

(58) Field of Classification Search
USPC ............. 5/601, 608, 600, 610, 616, 618; 297/135
See application file for complete search history.

(56) References Cited

U.S. PATENT DOCUMENTS

| | | | | |
|---|---|---|---|---|
| 4,190,774 A * | 2/1980 | Marinkovich et al. | ........ | 378/176 |
| 4,704,749 A * | 11/1987 | Aubert | ............... | 5/87.1 |
| 6,249,695 B1 * | 6/2001 | Damadian | ............... | 600/427 |
| 6,752,224 B2 * | 6/2004 | Hopper et al. | ............... | 180/22 |
| 6,817,363 B2 * | 11/2004 | Biondo et al. | ............... | 128/845 |
| 6,915,538 B2 * | 7/2005 | Treon | ............... | 5/611 |
| 8,260,517 B2 * | 9/2012 | Bhai | ............... | 701/70 |
| 2002/0088055 A1 * | 7/2002 | Vogel et al. | ............... | 5/600 |
| 2004/0098804 A1 * | 5/2004 | Varadharajulu et al. | ......... | 5/611 |
| 2004/0177445 A1 * | 9/2004 | Osborne et al. | ............... | 5/600 |
| 2005/0028280 A1 * | 2/2005 | Nakamura et al. | ............... | 5/601 |
| 2006/0150333 A1 * | 7/2006 | Harding | ............... | 5/618 |

FOREIGN PATENT DOCUMENTS

| | | |
|---|---|---|
| DE | 32 26 374 A1 | 1/1994 |
| DE | 694 23 842 T2 | 5/1995 |
| DE | 44 00 697 C 2 | 7/1995 |
| DE | 101 40 862 A1 | 4/2003 |
| DE | 103 54 739 A1 | 6/2004 |

OTHER PUBLICATIONS

German Office Action for DE 10 2006 008 505.1-45 dated Jan. 19, 2007 with English translation.

* cited by examiner

*Primary Examiner* — William Kelleher
*Assistant Examiner* — Myles Throop
(74) *Attorney, Agent, or Firm* — Lempia Summerfield Katz LLC

(57) ABSTRACT

A patient support table is provided. The patient support table includes a table plate that may be moved manually or by at least one motor having a control facility. At least one sensor is provided on the table plate. The at least one sensor is operable to determine a force exerted by a user on the table plate for table plate movement and produce a sensor signal. The at least one sensor is operable to communicate with the control facility of the motor. The control facility is operable to control the motor as a function of the sensor signal that is based on a predetermined reference force value such that the reference force value is not exceeded during the table movement.

20 Claims, 3 Drawing Sheets

PATIENT SUPPORT TABLE

This patent document claims the benefit of DE 10 2006 008 505.1 filed Feb. 23, 2006, which is hereby incorporated by reference.

BACKGROUND

The present embodiments relate to a patient support table.

Patient support tables with a table plate that is able to be moved manually and by at least one motor with an assigned control facility have been used, for example, in connection with x-ray devices, computer tomographs, or magnetic resonance devices. The table plate is adjustably supported relative to a table pedestal to allow movement. The patient lying on the table plate is able to be positioned in a desired or required manner relative to the x-ray device or a similar device.

The table plate may be moved manually, for example, when the table plate floats on its support unit. The table plate may also be moved automatically by a motor, for example, when a type of joystick or similar device is provided for control. Depending on the movement of joystick or similar device, an open-loop or closed-loop control facility controls the motor for corresponding plate movement.

A manually actuated clutch (switch) is provided to switch between motorized and manual plate movement. The clutch decouples the table plate from the drive train to the motor. The clutch is arranged behind the transmission in the drive train. This arrangement allows the user to avoid having to move the entire transmission during the manual table plate movement, which involves an additional even greater force effort than would have to be provided under normal circumstances.

During manual movement, a manual movement force is exerted and initiated exclusively by the users. The manual movement force depends on the weight of the patient lying on the table plate. A greater force is required to move a heavier patient than to move a lighter patient. The support unit should be constructed to permit great ease of movement, so that those who are not so strong are able to perform manual table plate movement for heavy patients. This construction is more complex and is associated with higher costs. The design of the clutch that decouples the table plate is also expensive and complex because the clutch is connected after the transmission, for example, in an area in which very high torque is already transmitted.

Generally, the table plate can only be moved manually with the table plate in a horizontal position. However, the table plate has to be frequently tilted/tipped to align the patient in the best possible way relative to the imaging device. In such cases, moving the plate manually is not possible, since the movement force to be exerted, for example, to raise the tilted/tipped table plate along with the patient, is very great and consequently cannot be managed. The only option here is automatic motorized plate movement which however can also be more time consuming and more complex.

SUMMARY

The present embodiments may obviate one or more of the drawbacks or limitations in the related art. For example, in one embodiment, a patient support table allows simple manual movement of the table plate and minimizes the force needed for movement.

In one embodiment, a patient support table includes a table plate, which can be moved manually and by at least one motor having an associated control facility. The patient support table includes at least one sensor that determines the force exerted by the user on the table plate for table plate movement. The force sensor communicates with the control facility of the motor. The control facility controls the motor depending on the sensor signal and takes into account a reference force value predetermined by a "host module" in accordance with the patient position. The reference force value is not exceeded during the table movement.

In one embodiment, an integrated sensor is provided on or in the table plate. The sensor directly measures the manual force exerted by the user for table plate movement. The sensor communicates with a closed-loop controller, which continuously receives the sensor signal and transmits the signal to the motor control facility. A reference force value is stored in this system. The reference force may serve as a comparison value or a measure value for the actual force value measured by the sensor.

When the actual force value measured by the sensor lies below the reference force value, the motor does not assist the displacement movement at all or only provides slight assistance When the reference force value is reached, the control facility controls the motor accordingly. The motor then operates to assist the tactile force exerted by the user, consequently operating in respect of the force in the same direction as the user wishes to move the table plate.

In one embodiment, the control parameters related to the actual situation are derived or determined for the motor from or on the basis of the measured actual force and the predetermined reference force value. For example, the measured force and the reference force value are the basis for specifying the setpoint value to the motor control. Because of the ongoing force measurement, the motor is controlled so that the reference force value is not exceeded. As the user increases the force introduced to move the table plate or accelerate the table plate, the drive force delivered by the motor transmitted to the table plate increases. The maximum force exerted by the user corresponds to the reference force value and no more force than that defined via this reference force value needs to be introduced.

In one embodiment, a closed-loop control includes a motor control that controls the motor depending on the actual force measured. When the measured actual force increases above the reference force value, the motor is immediately adjusted accordingly, in order to immediately reduce the measured force increase again, so that the maximum force that the user has to continuously exert during the displacement movement is the reference force. The adjustment or regulation may be undertaken in less than 100 microseconds.

In one embodiment, the reference force value is designed so that a specific table mass and table friction is quasi simulated to the user. The user applies a specific reference force to move the plate, the size of the force recalls the circumstances known previously to the user of the manually floating table plate movement with low load without motor assistance.

In one embodiment, the motor assistance that limits the reference force to be applied allows a simple displacement of the table plate independent of the patient load accommodated. The table plate may be manually moved in any direction, even with the plate in a tilted position. The table plate may be moved when in a tilted position because the reference force value is applied as the maximum upper force limit to be employed and the motor provides appropriate assistance. The reference force value does not represent a true comparison value for the actual force value. One or a number of control parameters are determined with reference to the reference force value such that the resulting motor assistance delivers the component of the force that is necessary, relative to the desired table movement obtained from the actual force measurement. The user only has to push using the limited reference force value as the maximum.

In one embodiment, a force is measured directly at the table plate. The force is measured by the sensor that is on or in the table plate.

In one embodiment, the at least one sensor is disposed in (on) a handle that is used by the user to move the table plate. A number of sensors may be provided in (on) each handle. The handle may include, for example, a knob type handgrip or railing that extends at least along sections of the table plate. The sensors provide redundancy with respect to force detection so that the control facility can balance the readings, or if one sensor fails, the reading from another sensor is always available. A force can be measured in the immediate vicinity of the location in which the tactile force is introduced if a number of sensors are distributed along a railing. Irrespective of where the one or more force sensors are actually arranged, the sensors are always positioned or disposed so that the force exerted directly by the user on the table plate is measured as a control value for the motor control facility.

In one embodiment, the at least one sensor may be a multi-axis sensor. The multi-axis sensor may be up to a 6-axis force sensor, for example, in the form of one or more expansion measurement strips. A multi-axis sensor is able to determine the direction of the force introduced, and from this direction the desired plate movement. Generally, a number of motors are provided. The motors move the table plate in different directions, for example, orthogonal to each other. The control facility for the motors can use the multi-axis sensor direction information about the force introduced to control the motors so that the motors apply the assisting motor force to the table plate precisely in the direction corresponding to the manual force direction. Optimized force assistance is possible.

In one embodiment, the sensor can determine the force and manually exerted torque on the table plate, which is tiltable around one or more axes. The control facility controls the motor based on a predetermined reference torque such that the reference torque is not exceeded.

In one embodiment, the sensor is also able to determine a torque for table plates that are tilted around a longitudinal or transverse axis. Depending on the weight of the patient without motor assistance, a different force effort is needed to provide the necessary rotational or tilting torque. One or more sensors are not only embodied for force determination, but also to determine the rotational or tilting torque exerted on the table plate in the relevant axis of rotation or pivot axis. A reference torque value is defined in advance as a reference or limit value and stored in the control facility. In one embodiment, when the sensor measurement indicates a force is being exerted on the table plate or is operating in the axis of rotation, the motor immediately provides assistance such that the excessive actual torque is compensated for by the motor and is made available by the latter. In the final analysis, the axis of rotation corresponds to the reference torque or lies slightly above it. The force applied by the user for tilting is limited to a reference force value. The user does not have to exert any more force to tilt the table plate than the defined reference force, regardless of how light or how heavy the patient actually is.

In one embodiment, different (multiple) motors may be used, depending on whether the support is for a purely axial plate movement or for a tilting of the plate. The control facility may assign the motors to different tasks or different directions of movement. Depending on the use of the patient support table, the motors are activated as a function of the recorded force or torque direction. The motors are activated to allow optimized motor assistance based on the defined reference force or reference torque values.

In one embodiment, the sensor for determining the force and also the torque is a multi-axis sensor, for example, a 6-axis force-torque sensor. The multi-axis sensor makes it possible to determine the direction of the force applied. The assisting force is appropriately aligned with the direction that the control facility activates the various motors. The assisting force depends on the activation of the various motors.

In one embodiment, the control facility is able to detect a collision between the table plate and another object. In another embodiment, a collision detection device is able to detect a collision between the table plate and another object and with the control facility controls the at least one motor as a function of the result of the collision determination. The motorized force assistance may be used for movement assistance and collision avoidance purposes. The control facility communicates, for example, with various virtual 3D movement models. Position or proximity sensors record whether the table plate, if continued to be moved at the given speed and in the given direction, would come too close to another object or result in a subsequent collision. For example, if the plate is moved relative to a C-arm x-ray device, there is always the danger of the plate colliding with the C-arm or with a solid-state radiation detector. The control facility continuously makes checks as to the collision situation, based on the sensor signals supplied and the plate movement detected. The plate movement detected is based on the actual force initiated by the user and the corresponding open-loop or closed-loop control parameters of the motors providing individual assistance. When a possible collision is determined, the control facility activates the motor or the motors such that the movement of the plate is slowly decelerated and the table plate is moved into a maximum permissible end position from which it cannot be moved any further in the direction of the collision. In the end position, the movement of the table plate is inhibited by the motors.

In one embodiment, when the braking begins and the user continues to attempt to move the table plate toward the collision position by pushing harder on the table plate, the actual force value exceeds the reference force value. However, the collision determination is given priority and the force exceeding the reference force value is ignored. The control of the motors is based on the collision determination result and the given movement parameters of the table plate. To move the table plate from its inhibited position, the user must, for example, first provide a release signal by pressing a button or a key so that the motor inhibition is canceled again.

In one embodiment, reference force values or reference torque values are assigned to the different recorded directions of movement of the table plate. The maximum force to be applied may be varied depending on the direction of movement. The user may be able to more quickly adapt to the real circumstances. For example, if the table plate is tilted around the transverse axis, an upwards movement of the table plate along the longitudinal plate axis can involve a greater force effort than a downwards movement. This inevitably matches the real sensitivity of the user who knows that considerably more force needs to be applied to lift the table plate than to push it downwards.

DETAILED DESCRIPTION

Figure 1:
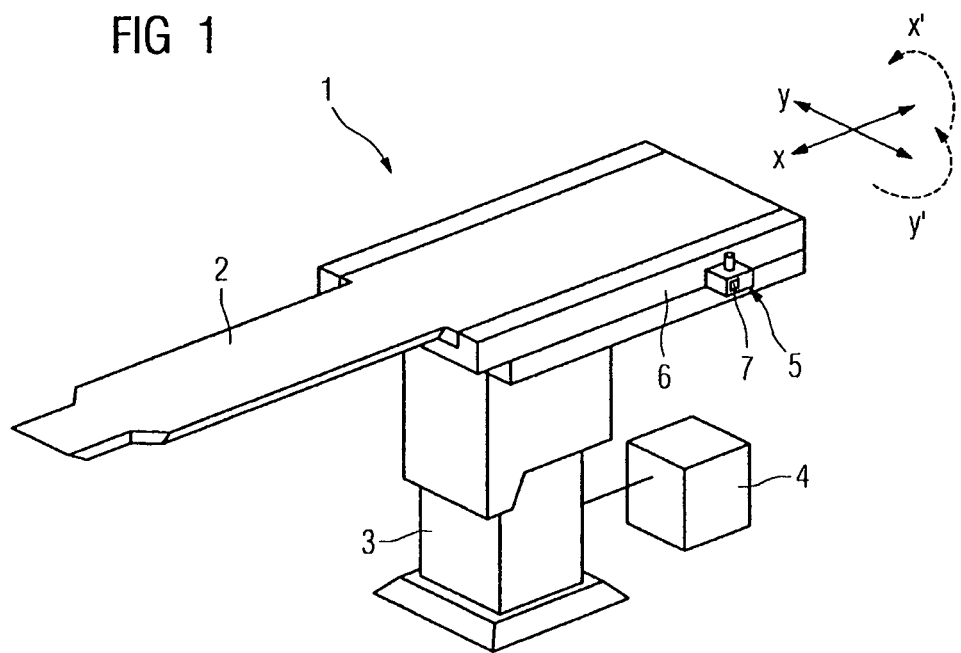
FIG. 1 is a perspective view of one embodiment of the patient support table.

In one embodiment, as shown in FIG. 1, a patient support table 1 includes a table plate 2. The table plate 2 may be moved in direction of movement x and in transverse direction y relative to pedestal 3. In some embodiments, the table plate 2 may be tilted around the table axes lying in the x or y direction. The tilting movement is shown in FIG. 1 by the dashed arrows labeled x' and y'.

In one embodiment, the patient support table 1 includes a control facility 4. The control facility 4 is used to control a number of motors. The table plate 2 can be moved automatically via the motors. The table plate 2 can also be moved manually.

In one embodiment, a patient support table 1 includes a handle 5. The handle 5 is disposed directly on the table plate 2, which in FIG. 1 includes a frame 6. The handle 5 may be gripped by users wishing to move the table plate manually. The handle 5 is also movement-coupled directly to the table plate 2. A force exerted on the handle 5 is introduced directly to the table plate 2.

In one embodiment, the handle 5 includes a grip that projects upwards and is able to be released from and fitted in different positions on the frame 6. The handle 5 includes a force sensor 7, which is, for example, a 3-axis sensor. The sensor 7 includes one or more expansion measurement strips or strain gauges that detect the force exerted by the user on the handle 5 and directly on the table plate 2. The sensor 7 is connected to the control facility 4, which continuously receives the sensor signal. The actual force that the user is applying is continuously present on control facility 4.

Figure 2:
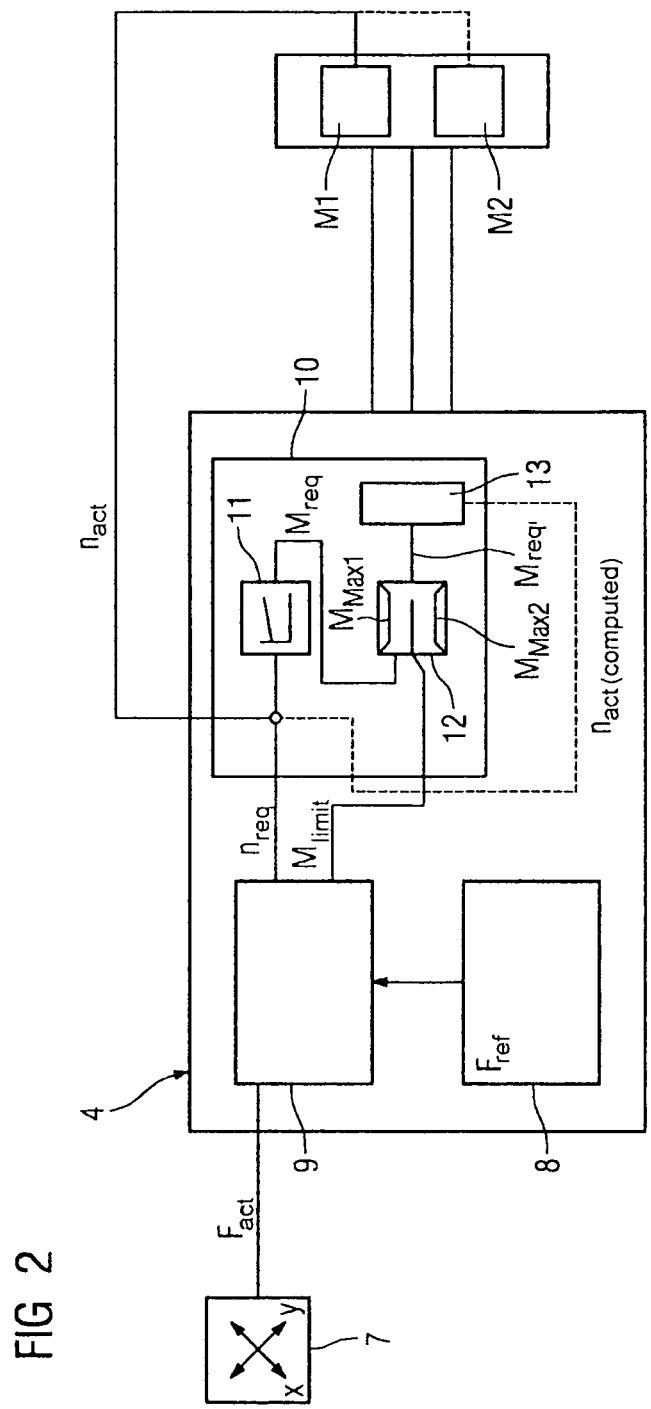
FIG. 2 a diagram that illustrates the major components of one embodiment of the control processes.

In one embodiment, as illustrated in FIG. 2, the force sensor 7 continuously determines the actual force Fact or outputs to the control facility 4 a corresponding sensor signal encoding this actual force Fact. The control facility 4, as shown in FIG. 2, includes a host module 8. Central working or operational parameters are used to control the movement of the table plate. The central working or operational parameters may be stored in the host module 8. The parameters can be entered via an appropriate input device or can be detected by the control facility 4 via a system of sensors 7 connected to the host module 8, for example, in the form of collision information or other suitable information. The host module 8 may be external to the control facility 4, but still be included in the table plate control.

In one embodiment, at least one reference force value $F_{ref}$ is stored in the host module 8. The reference force value defines the maximum force, for example, the greatest force able to be applied by the user, to move the table plate manually. The reference force may not be exceeded when the plate is being moved, which is achieved by a corresponding control of the movement motors.

In one embodiment, the control facility 4 includes a controller 9. The actual force Fact determined via the sensor 7 and the reference force value $F_{ref}$ is passed to the controller 9. The controller 9 derives a required speed value $n_{req}$ from the actual force $F_{act}$. This required speed value specifies the speed of the table plate that is to be achieved on application of the actual force, as initiated by the user.

In one embodiment, as illustrated in FIG. 2, a motor torque $M_{limit}$ is derived from the required speed by the controller 9. The motor torque $M_{limit}$ specifies the torque that the drive motor or motors must provide to achieve the required speed $n_{req}$ derived from the actual force $F_{act}$. The motor torque $M_{limit}$, is determined in the exemplary embodiment depicted in relation to two motors M1 and M2 shown in the diagram, provided for the x and y direction of movement. The controller 9 determines the direction of the applied force as resulting from separate x and y direction information from the signal of the sensor 7. The corresponding torque may also be determined for the separate motors M1 and M2. A resulting torque in the direction of the force exerted by the user is produced in the corresponding assigned drive.

In one embodiment, the motor torque $M_{limit}$ is determined based on the reference force value. If the actual force value $F_{act}$ is smaller than the reference force value $F_{ref}$ no control assistance via the motor system to reduce a force component exceeding the limit value $F_{ref}$ is necessary. For example, when the force effort applied by the user is below the maximum upper limit, no control assistance via the motor system to reduce a force component exceeding the limit value $F_{ref}$ is necessary. However, when the actual force $F_{act}$ of the acceleration is equal to or greater than the reference force value $F_{ref}$ a higher motor torque $M_{limit}$ is needed, whereon the motor torque $M_{limit}$ derived in the controller 9 from the required speed and the ratio $F_{act}$ to $F_{ref}$ is correspondingly increased. A user at most is required to provide a force corresponding to the reference force value.

In one embodiment, the determination of the motor torque is based on information provided by the host module 8 about any suitable forces that operate on the table plate 2. For example, the determination of the motor torque $M_{limit}$ is based on frictional forces or any downhill (rotational) forces produced by the table plate support when tilted during the movement around one of the axes. If the table plate, for example, is tilted around its y axis and pushed upwards (i.e. against the downhill force), a greater expenditure of force is necessary than for a movement in the opposite direction. The motor provides a considerably greater torque. The motor torque $M_{limit}$ is generated based on the predetermined reference force value $F_{ret}$ and the information for any given downhill force that results from or is derived from the plate position.

In one embodiment, frictional forces from the plate support are part of the determination of the motor torque $M_{limit}$. The greater the fictional forces are, the greater the force that has to be applied to move the table plate or to achieve or maintain the required speed. For example, the applied force is reflected in how the motor torque $M_{limit}$, to be provided is determined. In one embodiment, information provided by the host module 8 about a maximum permissible plate speed is also considered. The maximum permissible plate speed is used to determine the required speed since the required speed can at most correspond to the stored value of the maximum speed. The maximum speed indirectly impacts the generation of the motor torque $M_{limit}$.

In one embodiment, the two required values of the required speed $n_{req}$ and of the motor torque $M_{limit}$ are subsequently transmitted to a drive controller 10. The motor torque $M_{limit}$ may also be referred to as the situation-related maximum limit motor torque. The actual speed $n_{act}$ of the table plate 2 is transmitted to the drive controller 10. The actual speed $n_{act}$ and the required speed $n_{req}$ are processed in a speed controller (P1 controller) 11. The actual speed $n_{act}$ and the required speed $n_{req}$ are processed based on the deviation between the actual speed and the required speed. A required motor torque $M_{req}$ is determined by the speed controller 11.

In one embodiment, as shown in FIG. 1, a computed determination of the actual speed $n_{act}$ is based on the required values passed to the motor controller, as shown by the term "$n_{act}$ (computed)" in FIG. 2. The values $n_{req}$ and "$n_{act}$ (computed)" may then be processed in the P1 controller 11.

In one embodiment, the required motor torque $M_{req}$ is subsequently transmitted to a torque limiter 12. This unit also receives the motor torque (or maximum limit motor torque) $M_{limit}$. The torque limiter 12 may make two comparisons. The torque limiter 12 determines whether the required motor torque $M_{req}$ provided by the speed controller 11 is less than or equal to the motor torque $M_{limit}$. If motor torque $M_{req}$ is less than or equal to the motor torque $M_{limit}$, the required motor torque $M_{req}$ is output as the resulting required motor torque $M_{req}$ and transmitted to the device 13 which is used to determine the different required values for the motor voltage ($U_{req}$), the motor frequency ($f_{req}$), and the motor current ($I_{req}$). These parameters are then used to activate the two motors M1 and M2. The resulting required motor torque $M_{req}$ defines the torque to be applied based on the actual force provided and the peripheral conditions described above. The resulting required motor torque $M_{req}$ is able to provide motorized assistance for the table plate movement and to insure that the reference force value is undershot or at most retained.

When the required motor torque $M_{req}$ is greater than the motor torque $M_{limit}$, the output signal of the torque limiter 12 is limited to the motor torque $M_{limit}$ which corresponds to $M_{req}$. For example, when the torque of the motor is above $M_{limit}$, the motor does not provide the drive torque actually required. The motor does not provide the drive torque for only a very short time period. The user is for a very short time applying a force which is greater than $F_{ref}$. The motor does not achieve the required speed, but catches up again. The supporting plate acceleration via the motor compensates for this difference. The time span within which the user must push harder than predetermined $F_{ref}$ is extremely short.

In one embodiment, accounting for the motor torque $M_{limit}$, current is supplied by the drive control 10 to the relevant motor so that the same form of movement corresponding to the actual force measured by the force sensor 7 occurs. A direct "tactile response" is given to the operator such that when a greater force is applied the user also feels that the table plate is moving quickly. This is always done by taking into account the given reference force $F_{ref}$.

In one embodiment, the actual force $F_{act}$ and the corresponding control parameters for the motor or motors are continuously determined. An exact situation-related motor control that takes into account the actual and reference force values is possible.

In one embodiment, the control facility 4 accounts for any collision between the table plate 2 and other objects. For example, the host module 8 is linked to corresponding virtual 3D-movement models and/or collision sensors. The virtual 3D-movement models and/or collision sensors may detect an imminent collision by the table plate 2. The position may be continuously detected by the control facility 4 or may be derived from the corresponding drive parameters. The controller 9 is notified when the table plate 2 gets impermissibly close to another object. The controller 9 determines the corresponding values of the required speed $n_{req}$ and of the limit motor torque $M_{limit}$, and does this independently of the actual force $F_{act}$ detected. The motors are controlled with an ongoing delay of the table plate 2 movement, so that the table plate 2 is decelerated as required by the motors until it comes to a halt in order to avoid a collision. The ongoing delay is not based on the user, who has perhaps not noticed the possible collision, using a considerably higher force for further acceleration which lies above $F_{ref}$.

Figure 3:
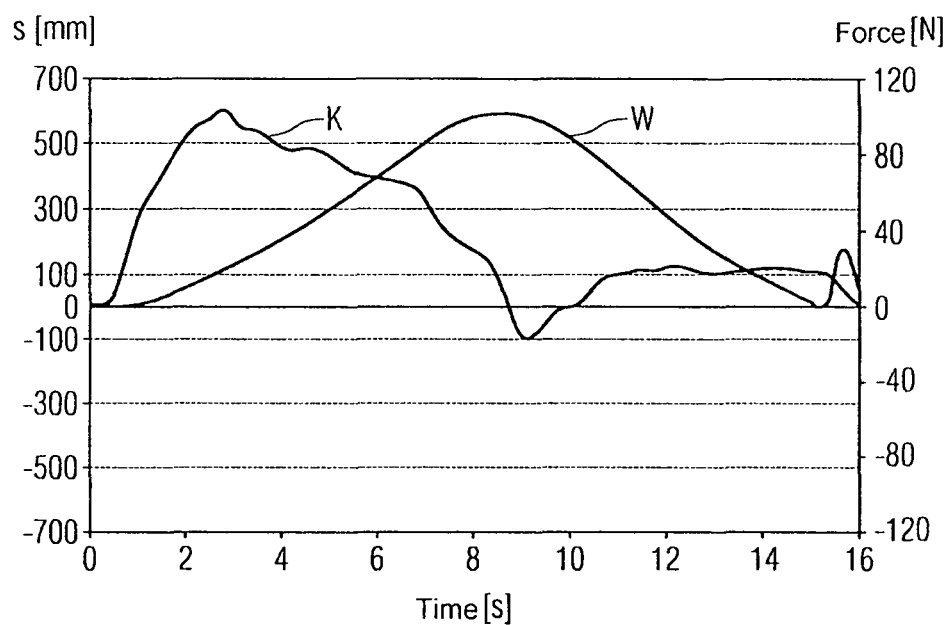
FIG. 3 is a diagram that illustrates the movement and force curves for one embodiment of a patient support table without motor assistance.
Figure 4:
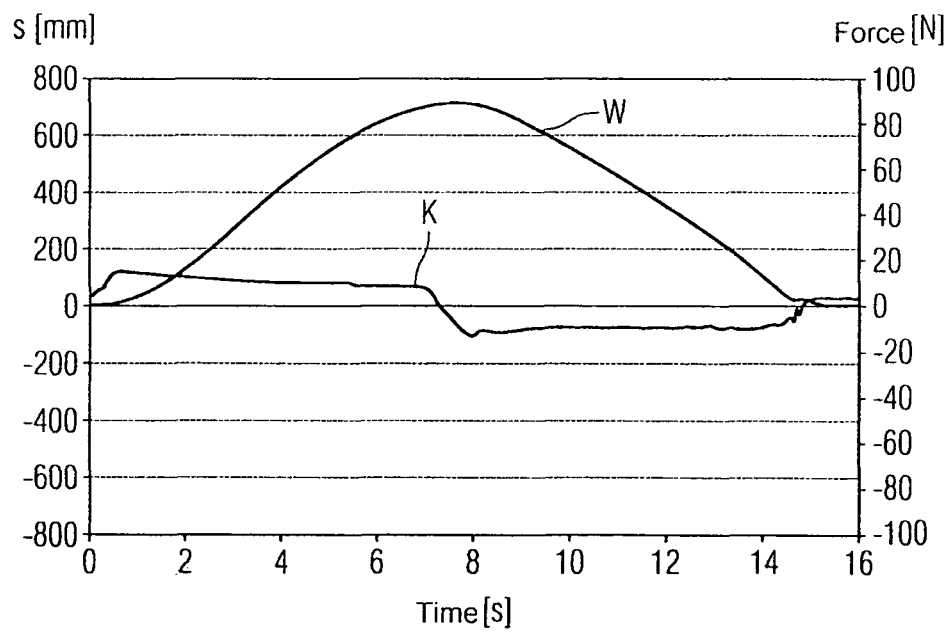
FIG. 4 is a diagram that illustrates the movement and force curves for one embodiment of a patient support table with motor assistance.

FIGS. 3 and 4 show two diagrams in which the movement path of the table plate for horizontal movement in the x direction and the force to be exerted for this are depicted. FIG. 3 illustrates the movement and force curves for one embodiment of a patient support table without motor assistance. FIG. 4 illustrates the movement and force curves for one embodiment of a patient support table with motor assistance. FIGS. 3 and 4 illustrate the situation for an assumed load of 300 kg on the table plate. The time s is plotted along the abscissa (horizontal axis) and the travel in mm or the force in N respectively along the two ordinates.

The relevant curve for the travel is labeled W in FIGS. 3 and 4. The curve for the actual force to be applied is labeled K. FIG. 3 illustrates when a user pushes the table plate bearing a load of 300 kg by applying a high force and a force peak of something over 100 N at the beginning of the plate movement, for example, when the table plate first has to be accelerated, after which the force curve drops off again. The curve K describes a minimum with a negative force effort. The table plate 2, being operated with a low force effort, is actively decelerated after the table plate 2 experiences an active frictional braking via the plate support, and is pushed into its end position.

FIG. 4 illustrates the force graph for a table plate 2 with motor assistance. The table plate 2 may be moved using a minimum force effort. In FIG. 4, an maximum force of 17 N is assigned. The force curve K, only reaches the maximum force at the beginning of the acceleration phase. The motor assistance immediately cuts in and the shape of the curve K is almost constant, up to the moment where active deceleration is applied and the force curve assumes negative values, and subsequently runs out.

As described with reference to FIG. 2, only a single reference force value is assigned. However, it would also be conceivable to provide different reference force values and to assign these to different table plate positions. For example, if the table plate is tilted around the y axis and if the table plate is to be moved upwards, the user may associate this with expending a greater force. To map this in a realistic manner for users, a higher reference force value could be assigned. Users must apply more force of their own until they experience the full motor assistance compared to moving the table plate horizontally.

A horizontal table plate movement has been described in the exemplary embodiments. A similarly embodied system is equally conceivable in connection with a tilting, swiveling, lifting, transverse and/or rotational movement of the table plate 2. The drive control may be embodied such that the rotation or tilting movement, which is exerted by users via their force initiated on the table plate, is detected via a sensor 7. The assisting motor torque that assists the tilting movement is determined via a corresponding signal processing unit. The determination prevents a reference force value or a reference torque value, which maps the reference force value, from being exceeded. When the table plate is tilted with the patient disposed on it, users only have to exert a maximum force defined in advance.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed:

1. A patient support table comprising:
a table plate operable to be moved manually and by at least one motor having a control facility; and
a handle disposed on the table plate, wherein a force exerted on the handle is introduced directly to the table plate, such that the handle is movement-coupled with the table plate;
at least one sensor provided in or on the table plate, or in or on the handle, the at least one sensor being operable to measure a force exerted manually by a user on the table plate for manual table plate movement and operable to produce a sensor signal,
wherein the at least one sensor is operable to communciate with the control facility of the motor, and
wherein the control facility is configured to control the motor as a function of the sensor signal based on a predetermined reference force value such that the control facility turns on the motor when the measured force exerted manually on the table plate via the handle during the table plate movement is greater than or equal to the reference force value.

2. The patient support table as claimed in claim 1, wherein the at least one sensor is a multi-axis sensor.

3. The patient support table as claimed in claim 1, wherein the at least one sensor is operable to determine the manually exerted force and torque exerted manually by the user on the table plate, the table plate operable to be tilted around one or more axes, the control facility being operable to control the motor based on a predetermined reference torque such that the predetermined reference torque is not exceeded.

4. The patient support table as claimed in claim 3, wherein the at least one sensor is a multi-axis sensor.

5. The patient support table as claimed in claim 1, wherein the control facility is operable to determine a collision between the table plate and another object, and control the motor depending on the result of the collision determination.

6. The patient support table as claimed in claim 1, wherein different recorded directions of movement of the table plate are assigned to different reference force or reference torque values.

7. The patient support table as claimed in claim 1, wherein the at least one sensor is disposed on the handle, and wherein the handle is holdable by the user to move the table plate.

8. The patient support table as claimed in claim 7, wherein the handle is a knob-type hand grip.

9. The patient support table as claimed in claim 7, wherein the handle is a first handle, and wherein the patient support table further comprises a plurality of second handles distributed on the table plate.

10. The patient support table as claimed in claim 2, wherein the at least one sensor is up to a 6-axis force sensor.

11. The patient support table as claimed in claim 4, wherein the at least one sensor is a 6-axis force sensor.

12. The patient support table as claimed in claim 7, wherein the at least one sensor is releasable from the handle.

13. The patient support table as claimed in claim 4, wherein the at least one sensor is disposed on the handle, and wherein the handle is holdable by the user to move the table plate.

14. The patient support table as claimed in claim 13, wherein the at least one sensor is releasable from the handle.

15. The patient support table as claimed in claim 7, wherein the handle is a railing that extends along the table plate.

16. The patient support table as claimed in claim 9, where the first handle includes at least one sensor, and each handle of the plurality of second handles includes at least one sensor.

17. The patient support table as claimed in claim 1, further comprising a collision device that is operable to determine a collision between the table plate and another object,
wherein the control facility is operable to control the motor depending on the result of the collision determination.

18. The patient support table as claimed in claim 5, wherein different recorded directions of movement of the table plate are assigned to different reference force or reference torque values.

19. The patient support table as claimed in claim 1, wherein the at least one sensor is operable to determine the manually exerted force or a torque exerted manually by the user on the table plate, the table plate operable to be tilted around at least one axis, the control facility being operable to control the motor based on a predetermined reference torque such that the predetermined reference torque is not exceeded.

20. The patient support table as claimed in claim 19, wherein the at least one sensor is a multi-axis sensor.

* * * * *